(12) United States Patent
Gao (10) Patent No.: US 10,004,872 B1
(45) Date of Patent: Jun. 26, 2018

(54) POSITIVE EXPIRATORY PRESSURE DEVICE HAVING AN OSCILLATING VALVE

(71) Applicant: Zhenping Gao, Eolia (CN)

(72) Inventor: Zhenping Gao, Eolia (CN)

(73) Assignee: D R Burton Healthcare, LLC, Farmville, NC (US)

( * ) Notice: Subject to any disclaimer, the term of this patent is extended or adjusted under 35 U.S.C. 154(b) by 578 days.

(21) Appl. No.: 14/640,713

(22) Filed: Mar. 6, 2015

(51) Int. Cl.
*A61M 16/20* (2006.01)
*A61M 16/06* (2006.01)

(52) U.S. Cl.
CPC ............ *A61M 16/20* (2013.01); *A61M 16/06* (2013.01)

(58) Field of Classification Search
CPC ............ A61M 16/0006; A61M 16/208; A61M 16/0057; A61M 16/0866; A61M 16/20; A61M 16/06; A61M 16/0003; A61M 16/0468; A61M 16/209; G01K 5/00
USPC .................................................... 128/207.16
See application file for complete search history.

(56) References Cited

U.S. PATENT DOCUMENTS

| 393,869 A | 12/1888 | Warren |
| 938,808 A | 11/1909 | Yount |
| 2,670,739 A | 7/1951 | McNeill |
| 2,918,917 A | 3/1955 | Emerson |
| 3,710,780 A | 1/1973 | Milch |
| 3,902,263 A * | 9/1975 | Schuman ............... F01B 11/00 60/517 |
| 3,908,987 A | 9/1975 | Boehringer |
| 4,054,134 A | 10/1977 | Kritzer |
| 4,062,358 A | 12/1977 | Kritzer |
| 4,182,366 A | 1/1980 | Boehringer |
| 4,198,969 A | 4/1980 | Virag |
| 4,221,381 A | 9/1980 | Ericson |
| 4,226,233 A | 10/1980 | Kritzer |
| 4,231,375 A | 11/1980 | Boehringer et al. |
| 4,267,832 A | 5/1981 | Hakkinen |
| 4,275,722 A | 6/1981 | Sorensen |
| 4,298,023 A | 11/1981 | McGinnis |
| 4,327,740 A | 5/1982 | Shuman |

(Continued)

FOREIGN PATENT DOCUMENTS

| EP | 0 372 148 | 6/1990 |
| EP | 0 678 306 | 10/1995 |

(Continued)

*Primary Examiner* — Gregory Anderson
*Assistant Examiner* — Margaret Luarca
(74) *Attorney, Agent, or Firm* — Tuggle Duggins P.A.; Blake Hurt (57) ABSTRACT

A PEP module is provided for producing and transmitting oscillations of expiratory air to the lungs and airways of a user to thereby loosen and mobilize mucus obstructions. The PEP module includes an external device housing having a mouthpiece at a first end thereof and a cover at an opposite second end thereof configured for providing resistance to the airflow of the expiratory air. The PEP module further includes a valve assembly contained within the external housing and disposed medially between the mouthpiece and the cover. The valve assembly includes a valve housing and a valve moveably mounted on the valve housing. The valve rapidly and repeatedly oscillates relative to the valve housing as the user exhales to produce oscillations in the expiratory air that are transmitted to the lungs and airways of the user to loosen and mobilize the mucus obstructions.

18 Claims, 3 Drawing Sheets

(56) References Cited

U.S. PATENT DOCUMENTS

| | | |
|---|---|---|
| 4,403,616 A | 9/1983 | King |
| 4,436,090 A | 3/1984 | Darling |
| 4,470,412 A | 9/1984 | Nowacki et al. |
| 4,601,465 A | 7/1986 | Roy |
| 4,611,591 A | 9/1986 | Inui et al. |
| 4,635,631 A | 1/1987 | Izumi |
| 4,651,731 A | 3/1987 | Vicenzi et al. |
| 4,739,987 A | 4/1988 | Nicholson |
| 4,770,413 A | 9/1988 | Green |
| 4,973,047 A | 11/1990 | Norell |
| 4,981,295 A | 1/1991 | Belman et al. |
| 5,018,517 A | 5/1991 | Liardet |
| 5,042,467 A | 8/1991 | Foley |
| 5,065,746 A | 11/1991 | Steen |
| 5,193,529 A | 3/1993 | Labaere |
| 5,345,930 A | 9/1994 | Cardinal et al. |
| 5,372,128 A | 12/1994 | Haber et al. |
| 5,381,789 A | 1/1995 | Marquardt |
| 5,451,190 A | 9/1995 | Liardet |
| 5,479,920 A | 1/1996 | Piper et al. |
| 5,540,220 A | 7/1996 | Gropper et al. |
| 5,569,122 A | 10/1996 | Cegla |
| 5,570,682 A | 11/1996 | Johnson |
| 5,598,839 A | 2/1997 | Niles et al. |
| 5,613,489 A | 3/1997 | Miller et al. |
| 5,645,049 A | 7/1997 | Foley et al. |
| 5,647,345 A | 7/1997 | Saul |
| 5,655,520 A | 8/1997 | Howe et al. |
| 5,658,221 A | 8/1997 | Hougen |
| 5,791,339 A | 8/1998 | Winter |
| 5,829,429 A | 11/1998 | Hughes |
| 5,848,588 A | 12/1998 | Foley et al. |
| 5,862,802 A | 1/1999 | Bird |
| 5,890,998 A | 4/1999 | Hougen |
| 5,893,361 A | 4/1999 | Hughes |
| 5,899,832 A | 5/1999 | Hougen |
| 5,910,071 A | 6/1999 | Hougen |
| 5,925,831 A | 7/1999 | Storsved |
| 6,026,807 A | 2/2000 | Puderbaugh et al. |
| 6,044,841 A | 4/2000 | Verdun et al. |
| 6,058,932 A | 5/2000 | Hughes |
| 6,066,101 A | 5/2000 | Johnson et al. |
| 6,067,984 A | 5/2000 | Piper |
| 6,083,141 A | 7/2000 | Hougen |
| 6,089,105 A | 7/2000 | Ricciardelli |
| 6,102,038 A | 8/2000 | DeVries |
| 6,167,881 B1 | 1/2001 | Hughes |
| 6,176,235 B1 | 1/2001 | Benarrouch et al. |
| D440,651 S | 4/2001 | Foran et al. |
| 6,240,917 B1 | 6/2001 | Andrade |
| 6,253,766 B1 | 7/2001 | Niles et al. |
| 6,293,279 B1 | 9/2001 | Schmidt et al. |
| 6,340,025 B1 | 1/2002 | Van Brunt |
| 6,345,617 B1 | 2/2002 | Engelbreth et al. |
| 6,412,481 B1 | 7/2002 | Bienvenu et al. |
| 6,500,095 B1 | 12/2002 | Hougen |
| 6,557,549 B2 | 5/2003 | Schmidt et al. |
| 6,581,595 B1 | 6/2003 | Murdock et al. |
| 6,581,596 B1 | 6/2003 | Truitt et al. |
| 6,581,598 B1 | 6/2003 | Foran et al. |
| 6,581,600 B2 | 6/2003 | Bird |
| 6,595,203 B1 | 7/2003 | Bird |
| 6,606,989 B1 | 8/2003 | Brand et al. |
| 6,607,008 B1 | 8/2003 | Yoshimoto et al. |
| 6,615,831 B1 | 9/2003 | Tuitt et al. |
| 6,631,721 B1 | 10/2003 | Salter et al. |
| 6,659,100 B2 | 12/2003 | O'Rourke |
| 6,702,769 B1 | 3/2004 | Fowler-Hawkins |
| 6,708,690 B1 | 3/2004 | Hete et al. |
| 6,708,691 B1 | 3/2004 | Hayek |
| 6,726,598 B1 | 4/2004 | Jarvis et al. |
| D490,519 S | 5/2004 | Pelerossi et al. |
| 6,776,159 B2 | 8/2004 | Pelerossi et al. |
| 6,848,443 B2 | 2/2005 | Schmidt et al. |
| 6,851,425 B2 | 2/2005 | Jaffre et al. |
| 6,904,906 B2 | 6/2005 | Salter et al. |
| 6,923,181 B2 | 8/2005 | Tuck |
| 6,929,007 B2 | 8/2005 | Emerson |
| 6,984,214 B2 | 1/2006 | Fowler-Hawkins |
| 7,059,324 B2 | 6/2006 | Pelerossi et al. |
| 7,096,866 B2 | 8/2006 | Be'eri et al. |
| 7,134,434 B2 | 11/2006 | Truitt et al. |
| 7,165,547 B2 | 1/2007 | Truitt et al. |
| 7,188,621 B2 | 3/2007 | DeVries et al. |
| 7,191,776 B2 | 3/2007 | Niles et al. |
| 7,191,780 B2 | 3/2007 | Faram |
| 7,214,170 B2 | 5/2007 | Sumners et al. |
| 7,383,740 B2 | 6/2008 | Krasilchikov et al. |
| 7,617,821 B2 | 11/2009 | Hughes |
| 7,699,054 B2 | 4/2010 | Pelerossi et al. |
| 7,717,847 B2 | 5/2010 | Smith |
| 7,771,472 B2 | 8/2010 | Hendricksen et al. |
| 7,779,841 B2 | 8/2010 | Dunsmore et al. |
| 7,798,148 B2 | 9/2010 | Doshi et al. |
| 7,856,979 B2 | 12/2010 | Doshi et al. |
| 7,909,033 B2 | 3/2011 | Faram |
| 8,006,922 B2 | 8/2011 | Katzer |
| 8,025,051 B2 | 9/2011 | Dagsland |
| 8,025,054 B2 | 9/2011 | Dunsmore et al. |
| 8,043,236 B2 | 10/2011 | Goldshtein et al. |
| 8,051,854 B2 | 11/2011 | Faram |
| RE43,174 E | 2/2012 | Schmidt et al. |
| 8,118,024 B2 | 2/2012 | DeVries et al. |
| 8,118,713 B2 | 2/2012 | Foley et al. |
| 8,225,785 B2 | 7/2012 | Richards et al. |
| 8,327,849 B2 | 12/2012 | Foley et al. |
| 8,460,223 B2 | 6/2013 | Huster et al. |
| 8,469,029 B2 | 6/2013 | Brown et al. |
| 8,485,179 B1 | 7/2013 | Meyer et al. |
| 8,539,951 B1 | 9/2013 | Meyer et al. |
| 8,985,111 B2 | 3/2015 | Grychowski et al. |
| D731,050 S | 6/2015 | Meyer |
| 9,149,589 B2 | 10/2015 | Meyer et al. |
| 9,220,855 B2 | 12/2015 | Meyer et al. |
| D776,804 S | 1/2017 | Meyer |
| D778,429 S | 2/2017 | Engelbreth et al. |
| D780,906 S | 3/2017 | Engelbreth et al. |
| 9,808,588 B1 | 11/2017 | Meyer et al. |
| 2003/0015195 A1 | 1/2003 | Haaije de Boer et al. |
| 2007/0259759 A1 | 11/2007 | Sumners et al. |
| 2008/0053456 A1 | 3/2008 | Brown et al. |
| 2008/0078383 A1 | 4/2008 | Richards et al. |
| 2009/0241949 A1 | 10/2009 | Smutney et al. |
| 2010/0101573 A1 | 4/2010 | Foley et al. |
| 2010/0139655 A1 | 6/2010 | Genosar et al. |
| 2010/0307487 A1 | 12/2010 | Dunsmore et al. |
| 2011/0290240 A1 | 12/2011 | Meyer et al. |
| 2012/0097164 A1 | 4/2012 | Rozario et al. |
| 2012/0304988 A1 | 12/2012 | Meyer et al. |
| 2013/0133649 A1 | 5/2013 | Grychowski et al. |
| 2013/0184619 A1* | 7/2013 | Von Hollen ......... A61M 16/00 601/46 |
| 2013/0312746 A1 | 11/2013 | Grychowski et al. |
| 2014/0041657 A1 | 2/2014 | Meyer et al. |
| 2014/0150790 A1 | 6/2014 | Meyer et al. |
| 2015/0013671 A1 | 1/2015 | Costella et al. |
| 2015/0053209 A1* | 2/2015 | Meyer ............... A61M 16/0006 128/205.24 |
| 2015/0151060 A1 | 6/2015 | Grychowski et al. |
| 2015/0224269 A1 | 8/2015 | Alizoti et al. |
| 2015/0297848 A1 | 10/2015 | Meyer et al. |
| 2015/0374939 A1 | 12/2015 | Meyer et al. |
| 2016/0136369 A1 | 5/2016 | Meyer et al. |
| 2016/0310695 A1 | 10/2016 | Meyer et al. |
| 2017/0028161 A1 | 2/2017 | Meyer et al. |
| 2017/0049979 A1 | 2/2017 | Meyer et al. |
| 2017/0128683 A1 | 5/2017 | Meyer et al. |

FOREIGN PATENT DOCUMENTS

| | | |
|---|---|---|
| EP | 1 103 287 | 5/2001 |
| EP | 1 435 251 | 7/2004 |
| EP | 1 464 357 | 10/2004 |
| EP | 1 897 576 | 3/2008 |

(56) References Cited

FOREIGN PATENT DOCUMENTS

| | | |
|---|---|---|
| EP | 1 908 489 | 4/2008 |
| EP | 2 444 114 | 4/2012 |
| EP | 2 455 137 | 5/2012 |
| GB | 2 425 488 | 11/2006 |
| WO | 1989 003707 | 5/1989 |
| WO | 1996 040376 | 12/1996 |
| WO | 1999 016490 | 4/1999 |
| WO | 2000 027455 | 5/2000 |
| WO | 2007 061648 | 5/2007 |
| WO | 2007 119104 | 10/2007 |
| WO | 2008 063966 | 5/2008 |
| WO | 2008 122045 | 10/2008 |
| WO | 2009 131965 | 10/2009 |
| WO | 2011 058470 | 5/2011 |
| WO | 2012 038864 | 3/2012 |
| WO | 2016 012740 | 1/2016 |

* cited by examiner

POSITIVE EXPIRATORY PRESSURE DEVICE HAVING AN OSCILLATING VALVE

FIELD OF THE INVENTION

The invention disclosed herein pertains generally to respiratory therapy devices, and more particularly pertains to a Positive Expiratory Pressure (PEP) module having an oscillating valve for enhancing the effectiveness of respiratory therapy.

BACKGROUND AND DESCRIPTION OF THE PRIOR ART

Many individuals suffer from pulmonary afflictions, such as Cystic Fibrosis (CF) and Chronic Obstructive Pulmonary Disease (COPD) that result in excess mucus production in the lungs and airways. Excess mucus secretions that obstruct respiratory airways and interfere with the ability of the individual to breathe must be cleared and expelled to prevent pneumonia, particularly following a surgical procedure. A common respiratory therapy for assisting an individual to loosen mucus secretions is known as Positive Expiratory Pressure (PEP). PEP is an airway clearance technique exercise that utilizes breathing resistance to generate positive pressure in the lungs and open airways. The positive pressure allows air to flow below the areas of mucus obstruction and move the obstructions from the smaller airways to the larger airways where the excess mucus can be expelled when the individual coughs. PEP therapy can also be used to promote deeper deposition of aerosol medication deeper into the lungs when combined with nebulized bronchodilator therapy. Additionally, PEP devices are beneficial to immobilized patients by providing means to exercise lung function and promote bronchial health.

A common PEP device, known as a PEP valve, has a mouthpiece that allows the user to draw air into the lungs through a one-way valve and subsequently blow the air out through a restricted channel, such as a small hole. The small hole causes resistance against exhalation that creates a positive pressure in the airways of the user, and consequently, an urge to cough. An enhanced PEP respiratory therapy known as oscillating PEP, also referred to as "flutter", utilizes a pipe-like device including a mouthpiece and an interior cone that cradles a steel ball sealed within a perforated cover. To perform the exercise, the user breathes in through the nose and exhales through the mouthpiece. As the user exhales, the ball oscillates within the sealed cone and the oscillations are transmitted throughout the user's airways to loosen and mobilize mucus obstructions during exhalations.

Another device, known in the art as an Acapella valve, combines PEP therapy with high frequency oscillation therapy. The Acapella valve includes a housing containing a lever having a magnet at one end. Air exhaled from the lungs of the user creates airflow through the Acapella valve that causes the lever to move back and forth inside the device. The device further includes magnetic means for adjustably varying the amount of resistance against exhalation, and consequently, the number and magnitude (i.e., frequency and amplitude) of the back and forth movements of the lever.

Yet another enhanced PEP respiratory therapy device is disclosed in U.S. Pat. No. 6,581,598 issued to Foran et al. and assigned to DHD Healthcare Corporation of Wampsville, N.Y., USA. The Foran et al. enhanced PEP respiratory device provides a variable frequency and variable magnitude positive pressure in the lungs and airways of the user utilizing a non-linear orifice for adjusting and maintaining a desired positive expiratory pressure oscillation according to a predetermined range of the pressure of the expiratory air exhaled by the user. The device includes a rocker assembly and a pivotal magnet support coupled to an adjustable orifice support that form a mechanism by which the discharge of expiratory air by the user is periodically interrupted to create a pulsating wave form. The frequency and magnitude of the pulsating wave form can be adjusted within the limits of the oscillating positive expiratory pressure therapy prescribed for the user.

The aforementioned PEP respiratory therapy devices, and in particular the existing devices for oscillating PEP therapy, are relatively complex in construction bulky, and oftentimes difficult to use, especially when being used to perform exercises to prevent pneumonia. As a result, the known devices are typically costly, cumbersome and prone to mechanical failure and misuse. It is apparent a need exists for an improved respiratory therapy device. A more particular need exists for an improved PEP module configured for use with oscillating positive expiratory pressure therapy. A still further need exists for an oscillating PEP therapy module of relatively simple construction that is economical, easy to use and less susceptible to mechanical failure and misuse.

In view of the problems, drawbacks, deficiencies and disadvantages associated with the existing PEP devices, the present invention was conceived and one of its objectives is to provide an improved PEP module for respiratory therapy or to perform exercises to prevent pneumonia.

It is another objective of the present invention to provide an improved PEP module configured for use with oscillating positive expiratory pressure therapy.

It is yet another objective of the present invention to provide an oscillating PEP module of relatively simple construction that is economical, easy to use and less susceptible to mechanical failure and misuse.

It is a further objective of the present invention to provide an oscillating PEP module for producing and transmitting oscillations of expiratory air to the lungs and airways of a user to loosen and mobilize mucus obstructions.

Various other objectives and advantages of the present invention will become apparent to those skilled in the art as a more detailed description of exemplary embodiments of the invention is set forth below.

SUMMARY OF THE INVENTION

The aforementioned, as well as other objectives not expressly set forth, are realized by providing an oscillating Positive Expiratory Pressure (PEP) module constructed according to the present invention, as shown and described by the exemplary embodiments disclosed herein. In one embodiment, the present invention provides a PEP module including a substantially hollow device housing having a mouthpiece at a first end thereof and a cover at an opposite second end thereof. The PEP device further includes a valve assembly configured to be disposed within the device housing medially between the mouthpiece and the cover. The valve assembly includes a valve housing and a flapper valve movably or rotatably mounted on the valve housing. The valve is operable for producing oscillations in the airflow of expiratory air exhaled by a user. The oscillations in the airflow of the expiratory air produced by the valve are transmitted to the lungs and airways of the user to enhance the process of loosening and mobilizing mucus obstructions in the lungs and airways. The mouthpiece is configured to receive the expiratory air exhaled by the user and the cover is configured to provide resistance to the airflow of the expiratory air and thereby generate a positive pressure in the lungs and airways of the user. The valve housing of the valve assembly defines a passageway for directing the airflow of the expiratory air exhaled by the user from the mouthpiece towards the cover. The valve is movable relative to the valve housing into and out of the airflow of the expiratory air directed by the passageway of the valve housing towards the cover. The airflow of the expiratory air directed by the passageway of the valve housing causes the valve to oscillate by virtue of the Venturi effect. The Venturi effect (generally described by the equation $P_1-P_2=P/2(v^2_2-v^2_1)$ where P is the density of the fluid, $v_1$ is the slower fluid velocity where the pipe is wider, and $v_2$ is the faster velocity where the pipe is narrower) is the phenomenon that occurs when a fluid (liquid or gas) flowing through a pipe is forced through a narrow section, resulting in a pressure decrease and a velocity increase which is mathematically described by the Bernoulli principle (generally described by the equation $v2/2+gz+P/\square$=constant where v is the fluid flow at a point in the fluid stream, g is the acceleration due to gravity, z is the elevation of the point above a reference plane, p is the pressure at a chosen point, and $\square$ is the density of the fluid at all points in the field.

In another embodiment, the present invention provides an oscillating PEP module for producing oscillations in expiratory air exhaled by a user and transmitting the oscillations to the lungs and airways of the user. The oscillating PEP module includes a generally hollow external device housing that has a mouthpiece at a first end thereof configured for receiving the expiratory air exhaled by the user and a cover at an opposite second end thereof configured for restricting the airflow of the expiratory air through the device housing and thereby generating a positive pressure in the lungs and airways of the user. The oscillating PEP module further includes a valve assembly contained within the external device housing and disposed medially between the mouthpiece and the cover. The valve assembly includes a valve housing defining a passageway therethrough for directing the expiratory air from the mouthpiece towards the cover, and a valve movably mounted on the valve housing and configured for repeated movement into and out of the airflow of the expiratory air. The valve is movable relative to the valve housing between a first position that is substantially out of the airflow of the expiratory air and a second position that is substantially in the airflow of the expiratory air. The airflow of the expiratory air directed by the passageway of the valve housing causes the valve to oscillate into and out of the airflow of the expiratory air by Bernoulli's principle. The repeated movement of the valve into and out of the airflow of the expiratory air produces oscillations in the expiratory air that are transmitted to the lungs and airways of the user by the positive pressure generated by the device to thereby loosen and mobilize mucus obstructions in the lungs and airways of the user.

In yet another embodiment, the present invention provides a method for producing oscillations of expiratory air exhaled by a user to the lungs and airways of the user. The method includes providing an oscillating Positive Expiratory Pressure (PEP) module including an external device housing having a mouthpiece at a first end thereof configured for receiving the expiratory air exhaled by the user and a cover at an opposite second end thereof for providing resistance to the airflow of the expiratory air through the device housing. The method further includes providing a valve assembly configured for being contained within the device housing and disposed medially between the mouthpiece and the cover. The valve assembly includes a valve housing defining a passageway for directing the airflow of the expiratory air from the mouthpiece towards the cover and a valve movably mounted on the valve housing above the passageway and configured for oscillating movement relative to the valve housing into and out of the airflow of the expiratory air through the passageway. The method further includes the user exhaling the expiratory air into the mouthpiece of the device housing such that the resistance to the airflow of the expiratory air provided by the cover generates a positive pressure in the lungs and airways of the user and causes the valve to produce oscillations in the airflow of the expiratory air that are transmitted to the lungs and airways of the user to loosen and mobilize mucus obstructions. The airflow of the expiratory air directed by the passageway defined by the valve housing causes the valve to oscillate into and out of the airflow of the expiratory air by Bernoulli's principle.

BRIEF DESCRIPTION OF THE DRAWINGS

The aforementioned aspects, objects, features, advantages and embodiments of the present invention will be more fully understood and appreciated when considered in conjunction with the accompanying drawing figures, in which like reference characters designate the same or similar parts throughout the several views.

DETAILED DESCRIPTION OF EMBODIMENTS OF THE INVENTION

Figure 1:
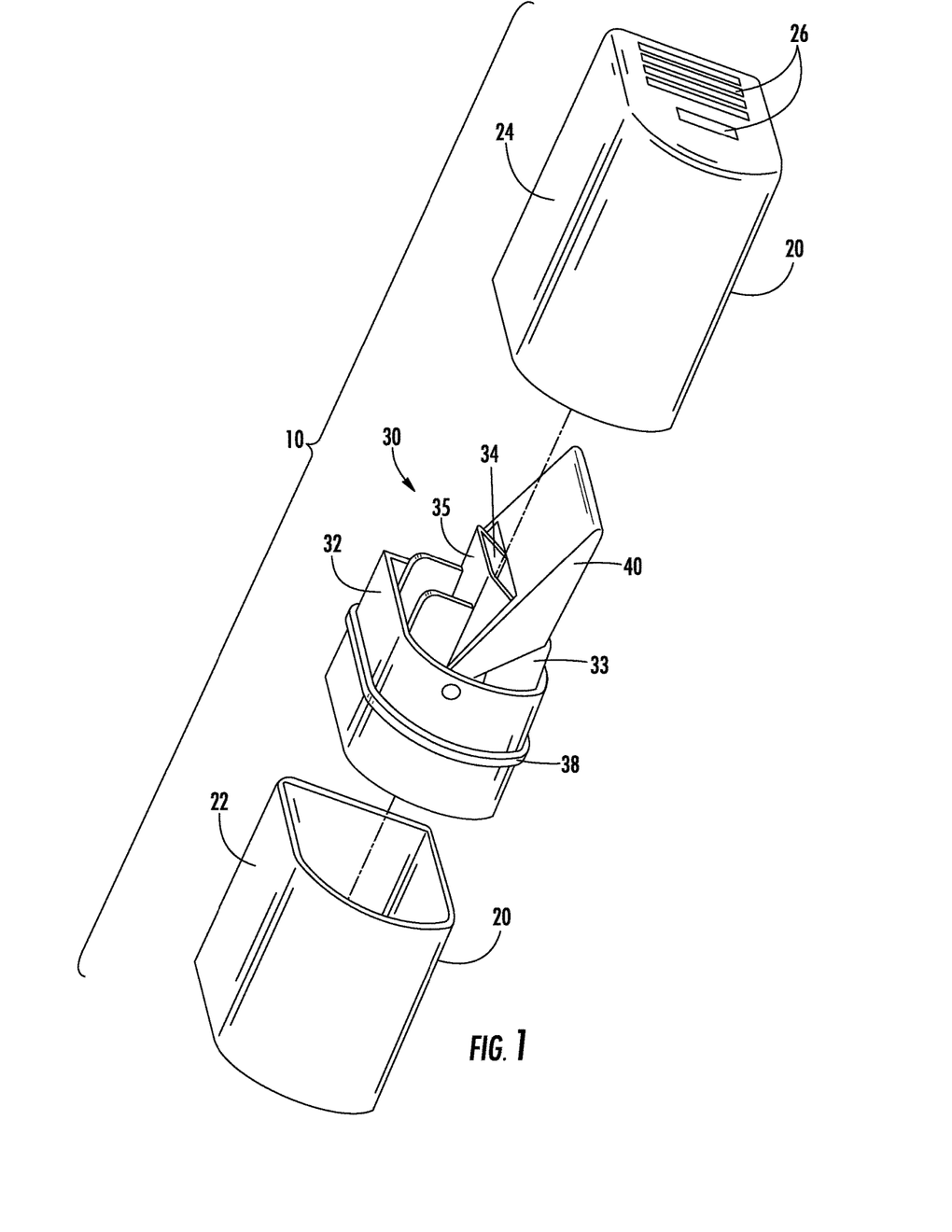
FIG. 1 is an exploded perspective view showing an exemplary embodiment of an oscillating Positive Expiratory Pressure (PEP) module constructed according to the present invention.

For a better understanding of the present invention and its operation, turning now to the drawings, FIG. 1 illustrates an exemplary embodiment of an oscillating Positive Expiratory Pressure (PEP) module, indicated generally by reference character 10, constructed according to the present invention. Oscillating (also referred to as "flapper") PEP module 10 is an enhanced respiratory therapy device for individuals that suffer from pulmonary afflictions, such as Cystic Fibrosis (CF) and Chronic Obstructive Pulmonary Disease (COPD). Oscillating PEP module 10 may also be utilized as an exercise to prevent pneumonia, for example in post-surgery patients and the elderly. Enhanced PEP transmits positive pressure oscillations produced by an oscillating PEP module throughout the user's airways, specifically the cilia lining the airway, to loosen and mobilize mucus obstructions during resistance generated by the device against expiratory air exhalations. Various structures and techniques are known for varying the magnitude and the frequency of the positive pressure oscillations transmitted to the lungs and airways of the user while exhaling expiratory air.

As shown in the embodiment of FIG. 1, the oscillating PEP module 10 comprises an external device housing 20 configured for containing an oscillating valve assembly 30 disposed within the device housing, preferably but without limitation located medially between a mouthpiece 22 and a cover 24. Device housing 20 is substantially hollow for containing the valve assembly 30 and thus, as shown herein, is preferably elongated and generally rectangular. However, device housing 20 may have any desired size and shape suitable for being comfortably held and manipulated by a user, particularly with a single hand. If desired, the components of the PEP module 10, including the mouthpiece 22, the cover 24 and the valve assembly 30, are made of a lightweight and relatively inexpensive material, such as molded plastic, for example polypropylene or polyethylene. Regardless, the mouthpiece 22 has a portion (not shown) configured for being engaged by the mouth of the user in a manner that allows the user to comfortably exhale expiratory air into the substantially hollow device housing 20 and subsequently through the valve assembly 30 to the cover 24. Cover 24 is provided with one or more apertures, openings or the like 26, configured for allowing the expiratory air exhaled by the user to be discharged into the ambient atmosphere. In the exemplary embodiment of the device housing 20 illustrated herein, openings 26 are configured as a plurality of generally parallel slots. If desired, mouthpiece 22 and cover 24 may be sealed around the valve assembly 30. In a preferred embodiment, however, at least one of the mouthpiece 22 and the cover 24 is removably affixed to the valve assembly 30 so that the valve assembly may be accessed and/or removed for cleaning and/or replacement. An alternate embodiment of PEP device 10 may further include a top positioned proximate valve assembly 30 with a downward depending finger (not shown) configured for selective engagement with valve 40 during use. It would be understood that such an accessory may be used to frictionally vary the rotation of valve 40 during use, permitting greater flexibility in the frequency and amplitude of the oscillations experienced by the user, for example for users that had variable expiratory capacities such as the very young or the infirm. Embodiments of the finger may be flat and straight across, may define a slope from one end to the other, or may define an arcuate face.

Figure 2:
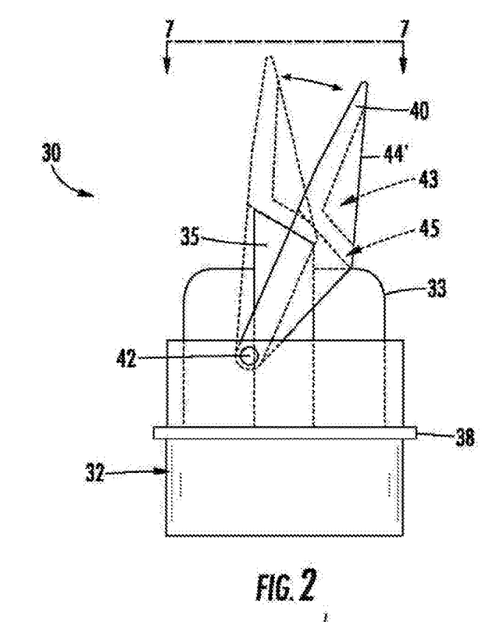
FIG. 2 is an elevated side view showing the valve assembly of the oscillating PEP module of FIG. 1, the opposite side view being reverse, but substantially identical to the elevation view shown in FIG. 2.
Figure 3:
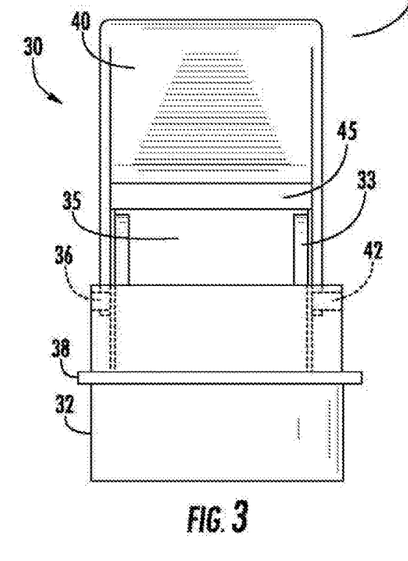
FIG. 3 is a top plan view of the valve assembly shown in FIG. 2.
Figure 4:
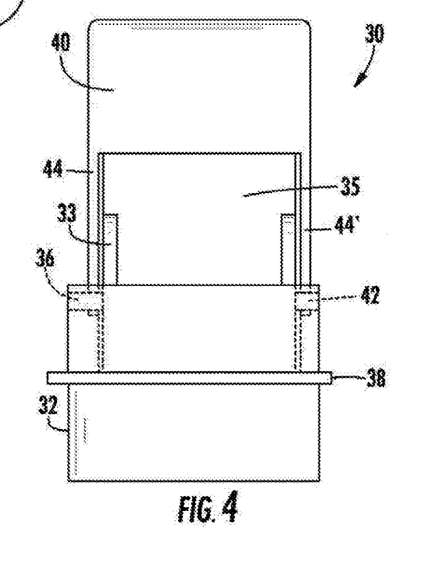
FIG. 4 is a bottom plan view of the valve assembly shown in FIG. 2.
Figure 5:
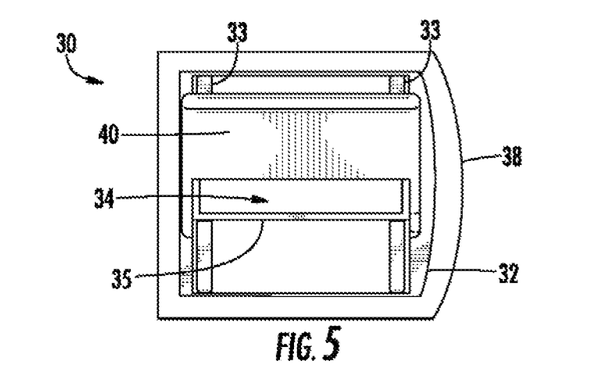
FIG. 5 is an elevated end view of the valve assembly shown in FIG. 2.
Figure 6:
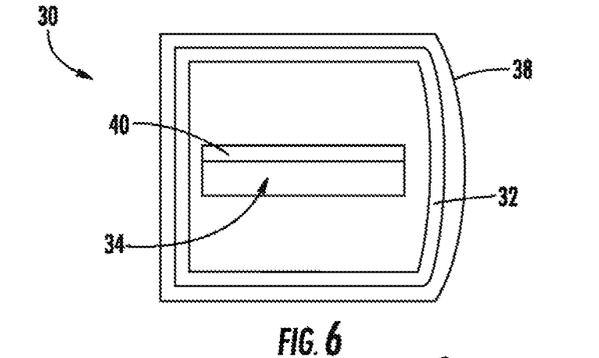
FIG. 6 is an opposing elevated end view of the valve assembly shown in FIG. 5.
Figure 7:
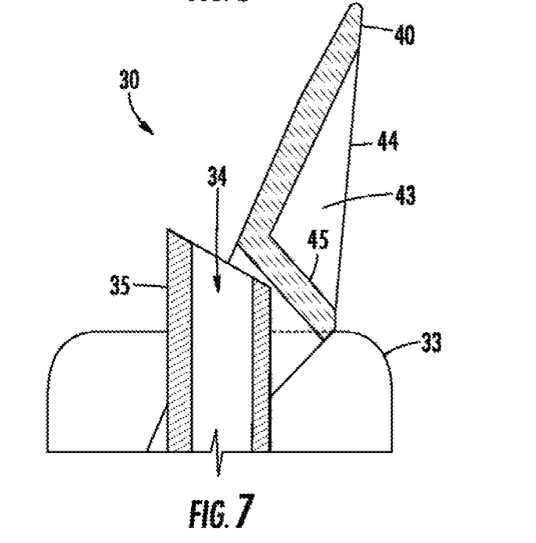
FIG. 7 is a sectional view taken along the line 7-7 in FIG. 2 showing the oscillating valve of the valve assembly in greater detail.

FIGS. 2-6 show elevated side, top, bottom, and end views of the oscillating valve assembly 30. FIG. 7 is a sectional view taken from FIG. 2 showing the valve assembly 30 in greater detail. The oscillating valve assembly 30 comprises a valve housing 32 defining passageway 34 therethrough and a valve 40 movably disposed overtop passageway 34 on the valve housing 32. Valve 40 is shaped generally as an "H" shape having a lower portion open such that the lower legs straddle passageway 34 and the opposing upper portion is closed off or solid between the upper legs creating a "sail". The legs 44, 44' (FIGS. 4 and 7) of valve 40 as seen in FIG. 2 are triangular in shape and as understood are in opposing, parallel position with a central horizontal ledge 45 (FIGS. 3 and 7) angularly disposed therebetween which complements the outermost angular portion formed by wall(s) 35 of passageway 34 when positioned thereabove. As shown herein, the valve housing 32 is generally rectangular and configured (i.e., sized and shaped) to be received within the device housing 20 of the oscillating PEP device 10. Valve housing 32 defines an open channel or passageway 34 (FIG. 1) defined by surrounding wall(s) 35 for communicating the expiratory air exhaled by the user into the mouthpiece 22 of the oscillating PEP device 10 through the valve assembly 30 to the cover 24. As would be understood surrounding wall(s) 35 as shown in FIGS. 5 and 6 creates rectangular passageway 34 however could be formed to take any size or shape such as square, circular or otherwise so long as it limits or narrows the pathway of expiratory air passing through mouthpiece 22, valve assembly 30 and cover 24. The remainder of valve housing 32 is essentially closed or solid to restrict the passage of expiratory air through passageway 34. Valve housing 32 is further provided with at least one aperture, opening, recess or the like 36 configured (i.e., sized and shaped) to receive a corresponding post, peg, protrusion 42 or the like defined on an exterior surface of valve 40, as will be described in greater detail hereafter. Valve housing 32 may further comprise a ledge, ridge, rib 38 or the like that extends radially outwardly from the valve housing to locate and seat the mouthpiece 22 on one end of the valve housing, and to likewise locate and seat the cover 24 on the other opposite end of the valve housing, creating a seal and preventing any leakage of expiratory air. If desired, the mouthpiece 22 and the cover 24 may engage an exterior surface of the valve housing 32 in an interference fit, such that at least one of the mouthpiece and the cover is removable from the valve housing to thereby provide access to the valve housing for cleaning, removal and/or replacement. An alternate embodiment of PEP device 10 may include an attachment member such as a gasket (not shown) to further solidify one or more connections between mouthpiece 22, cover 24, and valve housing 32.

Valve 40 is movably, and preferably rotatably, disposed on the valve housing 32. In the embodiment shown and described herein, valve 40 is mounted on the valve housing 32 for pivoting movement indicated by the curved, double-headed arrow in FIG. 2. More particularly, valve 40 is operable for movement into and out of the airflow of the expiratory air directed through the passageway 34 defined by the valve housing 32 between respectively the position of the valve shown primarily in broken line and the position of the valve shown in solid line. As previously mentioned, valve housing 32 has at least one opening, recess 36 or the like formed therein for receiving a corresponding peg, post, protrusion 42 or the like formed on the valve 40 in pivoting relationship. Preferably, valve housing 32 has a pair of opposite openings 36 and valve 40 has a corresponding pair of opposite posts 42 configured to be relatively loosely received within the openings, such that the valve pivots freely between the two extreme positions illustrated in FIG. 2. It will be readily apparent to those skilled in the art that the valve housing 32 could be provided with at least one suitable peg, post, protrusion or the like and the valve 40 could be provided with at least one opening, recess or the like in a similar manner to achieve the same result. For purposes of the present disclosure, any combination and/or arrangement of structure that permits movement of the valve 40 relative to the valve housing 32 into and out of the airflow in the manner described herein is intended to be encompassed by suitable embodiments of an oscillating PEP module 10 according to the invention.

It should be noted that valve 40 is limited in pivoting movement between the extreme positions illustrated in FIG. 2. By way of example only and not limitation, valve housing 32 may be provided with seat(s) 33 configured for limiting the travel of the valve 40 in the direction away from passageway 34. Similarly, valve 40 may have an opening, notch, or recess formed therein defining a generally hollow cavity or interior 43 (FIGS. 2 and 7) above the central horizontal ledge of valve 40 that is configured to overlay the passageway 34 of the valve housing 32 when the valve is aligned with the passageway. As a result, valve 40 frictional engages the bottom of the angled exterior structure of the passageway 34 by virtue of their complementary (meaning that the sum of their respective angles equals one hundred eighty degrees)(180°) angular cross-sections to limit the travel of the valve in the direction of the passageway. While the respective angles may vary, an embodiment of valve 40 defines an angle greater than ninety degrees (90°) with a housing 32 defining an angle less than ninety degrees (90°) relative to a vertical axis. A more preferred embodiment includes valve 40 that defines an angle greater than one hundred degrees (100°) and housing 32 defines an angle less than eighty degrees (80°), respectively. In the position of the valve 40 indicated in FIG. 2 by solid lines (also as shown in FIG. 1), at least a portion of the passageway 34 of the valve housing 32 is open as also seen in FIGS. 5 and 6 to deliver expiratory air exhaled by the user to the cover 24 of the external housing 20 of the module 10. With respect to the complementary angles defined by valve 40 and passageway 34, the nature of the angles maintains the respective component surfaces in close proximity throughout a portion of the pivoting action of valve 40 during use. In an alternate embodiment, the distance between valve 40 and passageway is within the range of a quarter to three millimeters (0.25-3.0 mm), and preferably is less than one and a half millimeters (1.5 mm) for about the first forty-five degrees (45°) of rotation of the "flapping" of valve 40, at which point valve 40 clears the beveled top edge of the passageway.

In operation, a user holds the oscillating PEP module 10 at a comfortable location and positions his or her lips around an inlet member in direct or indirect fluid communication with the mouthpiece 22 of the device housing 20 with the PEP device directed outwardly away from the his or her mouth, or through an accessory tube piece (not shown) attached to the mouthpiece 22. The user inhales ambient air through his or her nose, or alternatively, through his or her mouth around the mouthpiece 22 of the device housing 20. The user then exhales expiratory air (i.e., air from the user's lungs and airways) through the mouthpiece 22 of the device housing 20 of the PEP device 10. The cover 24 operates to restrict the flow of the expiratory air out of the device housing 20 through the one or more constricting openings 26 formed in the cover. As a result, the user experiences rhythmic resistance to the exhalation of the expiratory air, and consequently, a corresponding positive pressure in his or her lungs and airways by virtue of the motion of valve 30. The positive pressure in the user's lungs and airways loosens and mobilizes mucus obstructions from the lungs and smaller airways and moves the mucus obstructions to the larger airways from where they can be subsequently coughed out by the user.

Operation of the oscillating PEP device 10 is enhanced by the valve assembly 30 disposed within the device housing 20, and more particularly, by the valve 40 movably and pivotably mounted on the valve housing 32 of the valve assembly. In one embodiment, the expiratory air exhaled by the user is directed through the passageway 34 defined by the valve housing 32, rotatably displacing the movable valve 40. The flow of expiratory air over the surface of valve 40 creates a lifting force, which causes the valve to move from a first position indicated in FIG. 2 by the broken lines towards a second position indicated in FIG. 2 by the solid lines. The force necessary to displace valve 40 is relatively light compared to the prior art, allowing valve 40 to move freely into and out of the air stream as described, even if used by children or the elderly. As the valve 40 moves towards the second position over the passageway 34 defined by the valve housing 32, the expiratory air passing beneath valve 40 creates a lower pressure than the ambient air above valve 40, commonly referred to as a Venturi effect and Bernoulli principle, and is pulled thereby towards the first position. The process repeats rapidly and continuously as the user exhales the expiratory air through the device housing 20 of the PEP device 10. As a result, the valve 40 oscillates back and forth during exhalations of the expiratory air. More particularly, the valve 40 moves rapidly and repeatedly into and out of the airflow of the expiratory air being exhaled through the PEP module 10 by the user. The oscillations of the valve 40 produce oscillations in the airflow of the expiratory air that are transmitted back to the user's lungs and airways via the cyclical positive pressure generated by the PEP module 10. An embodiment of PEP module 10 has been tested and recorded to produce in excess of ten centimeters (10 cm) of water (H2O) of positive end exhalation pressure (PEEP), and has been observed to produce as much as twelve centimeters (12 cm) of water (H2O) of PEEP as a maximum, far in excess of the three to four centimeters (3-4 cm) of water (H2O) PEEP observed by prior art devices. The oscillations in the positive pressure transmitted to the lungs enhances the process of loosening and mobilizing mucus obstructions without the requirement of an enclosed and/or pressured module environment, and thereby increase the effectiveness of the respiratory therapy exercise provided by the oscillating PEP module 10.

It should be noted that the magnitude and frequency of the oscillations of the valve 40 may be adjusted as desired in various ways, in addition to the embodiment of PEP module 10 including a top as previously described. In one embodiment, the valve 40 may be biased in the direction of the first position, such as by a torsional spring having one end in engagement with the valve housing 32 and the other opposite end in engagement with the valve. In this manner, the intensity of the oscillations of the valve 40 would be increased, while the frequency of the oscillations of the valve would be reduced. In another embodiment, the size of the interior of the valve 40 may be increased relative to the size of the passageway 34 defined by the valve housing 32 to reduce the number of back-and-forth movements of the valve into and out of the airflow for a given volume of expiratory air exhaled by the user. In yet another embodiment, the extent of the travel between the first and second positions of the valve 40 (i.e. the range of motion of the valve) may be increased to reduce the frequency of the oscillations of the valve, or conversely, may be reduced to increase the frequency of the oscillations of the valve. Regardless, it is intended that all such modifications to the valve 40 and/or the valve housing 32 of the valve assembly 30, as well as others that will be readily apparent to those having skill in the art, are considered to be within the scope of the present invention.

It should be noted and will be readily apparent to and understood and appreciated by those skilled in the art that the drawings, figures, illustrations and examples provided herein are for explanatory purposes only and are not intended to limit the scope of the following appended claims.

I claim:

1. A Positive Expiratory Pressure (PEP) module comprising:
   an airflow passageway formed from a device housing and a valve housing, the airflow passageway having a first end and an opposing second end; and
   a valve assembly configured to be disposed between the first and second airflow passageway ends, the valve assembly comprising the valve housing and a valve movably mounted on the valve housing, the valve defined by first and second legs movably affixed to the valve housing, the first and second legs joined by a central ledge, the central ledge defining an angle that is complementary to an angle defined by a wall that forms a portion of the airflow passageway, whereby the valve is operable for producing oscillations in an airflow, whereby the valve is configured to pivot between a first posture substantially in the airflow whereby the valve is positioned more proximal the airflow passageway and oriented complementary thereto, and a second posture substantially out of the airflow whereby the valve is pivoted more distal relative to the airflow passageway, and whereby the valve assumes the first posture absent the presence of the airflow.

2. The PEP module according to claim 1, wherein the device housing second end has at least one opening formed therethrough.

3. The PEP module according to claim 1, wherein the valve oscillates repeatedly between the first posture and the second posture.

4. The PEP module according to claim 3, wherein the airflow of the expiratory air directed by the airflow passageway causes the valve to oscillate via a Venturi effect and Bernoulli's principle.

5. The PEP module of claim 4, wherein the first and second legs define a triangular cross-sectional shape.

6. The PEP module of claim 4, wherein the valve defines a generally hollow interior.

7. The PEP module of claim 4, wherein a section of the airflow passageway is defined by a valve wall with an angular outermost portion, and wherein the central ledge is angularly disposed relative to the wall angular outermost portion, such that the central ledge and the wall angular outermost portion are complementary to one another in the valve first posture.

8. The PEP module of claim 7, wherein the wall angular outermost portion defines an angle of less than ninety degrees (90°) and the central ledge defines an angle of more than ninety degrees (90°).

9. The PEP module of claim 7, wherein a distance separating the wall angular outermost portion and the central ledge is between a quarter of a millimeter and three millimeters (0.25 mm-3.0 mm).

10. The PEP module of claim 7, wherein the valve housing defines a seat configured for limiting the travel of the valve in a direction away from the passageway.

11. The PEP module of claim 7 further comprising an annular rib extending radially outwards from the valve housing, wherein the annular rib is operable to seat the mouthpiece on an end of the valve housing, and wherein the annular rib is operable to seat the cover on an opposing end of the valve housing relative to the mouthpiece.

12. The PEP module of claim 7, wherein each of the first and second legs define a post, and wherein the valve housing defines corresponding recesses for pivotably receiving different ones of the posts therein, and wherein the valve housing further defines a seat configured to limit the travel of the valve away from the passageway.

13. The PEP module according to claim 1, wherein the valve housing comprises a radially outwardly extending rib for locating and seating at least one of the first and second device housing ends on the valve assembly.

14. An oscillating Positive Expiratory Pressure (PEP) module for producing oscillations in expiratory air exhaled by a user and transmitting the oscillations to the lungs and airways of the user, the oscillating PEP module comprising:
   a generally hollow external device housing, the device housing comprising:
   a mouthpiece at a first end thereof configured for receiving the expiratory air; and
   a cover at an opposite second end thereof configured for restrictively releasing the airflow of the expiratory air through a device housing airflow passageway generating a positive pressure in the lungs and airways of the user; and
   a valve assembly contained within the external device housing and disposed medially between the mouthpiece and the cover, the valve assembly comprising:
   a valve housing defining a valve housing airflow passageway therethrough for directing the expiratory air from the mouthpiece towards the cover, the valve housing airflow passageway in fluidic communication with the device housing airway passageway; and
   a valve movably mounted on the valve housing and configured for repeated movement into and out of the airflow of the expiratory air, the valve defined by first and second legs positioned in parallel orientation and rotatably affixed to the valve housing at opposing sides of the valve housing airflow passageway, the first and second legs joined by a planar central ledge, the central ledge defining an angle complementary to an angle defined by a wall that forms a terminal portion of the passageway of the valve housing, whereby the valve is configured to pivot between a first posture substantially in the airflow of expiratory air whereby the valve is positioned more proximal the valve housing airflow passageway and oriented complementary thereto, and a second posture substantially out of the airflow of expiratory air whereby the valve is pivoted more distal relative to the valve housing airflow passageway, and whereby the valve assumes the first posture absent the presence of the expiratory airflow.

15. The oscillating PEP module according to claim 14, wherein the airflow of the expiratory air directed by the passageway of the valve housing causes the valve to oscillate into and out of the airflow of the expiratory air via a Venturi effect and Bernoulli's principle.

16. A method for producing oscillations of expiratory air exhaled by a user to the lungs and airways of the user, the method comprising:
   providing the PEP module of claim 14; and
   the user exhaling the expiratory air into the mouthpiece of the device housing such that the resistance to the airflow of the expiratory air provided by the cover generates a positive pressure in the lungs and airways of the user and causes the valve to produce oscillations in the airflow of the expiratory air that are transmitted to the lungs and airways of the user to loosen and mobilize mucus obstructions.

17. The method according to claim 16, wherein the valve is pivotally mounted on the valve housing and wherein the oscillations in the airflow of the expiratory air are produced by pivoting movement of the valve into and out of the airflow of expiratory air directed by the passageway defined by the valve housing.

18. The method according to claim 17, wherein the airflow of the expiratory air directed by the passageway defined by the valve housing causes the valve to oscillate into and out of the airflow of the expiratory air by a Venturi effect and Bernoulli's principle.

\* \* \* \* \*